(12) United States Patent
Stitt et al.

(10) Patent No.: US 10,400,036 B2
(45) Date of Patent: *Sep. 3, 2019

(54) COMPOSITIONS AND METHODS FOR INCREASING MUSCLE MASS AND MUSCLE STRENGTH BY SPECIFICALLY ANTAGONIZING GDF8 AND OR ACTIVIN A

(71) Applicant: Regeneron Pharmaceuticals, Inc., Tarrytown, NY (US)

(72) Inventors: Trevor Stitt, Ridgewood, NJ (US); Esther Latres, New York, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/893,480

(22) Filed: Feb. 9, 2018

(65) Prior Publication Data

US 2018/0171006 A1    Jun. 21, 2018

Related U.S. Application Data

(63) Continuation of application No. 15/282,489, filed on Sep. 30, 2016, which is a continuation of application No. 15/077,662, filed on Mar. 22, 2016, now abandoned, which is a continuation of application No. 14/496,941, filed on Sep. 25, 2014, now abandoned, which is a continuation of application No. 13/676,233, filed on Nov. 14, 2012, now Pat. No. 8,871,209.

(60) Provisional application No. 61/559,175, filed on Nov. 14, 2011, provisional application No. 61/607,024, filed on Mar. 6, 2012, provisional application No. 61/661,451, filed on Jun. 19, 2012.

(51) Int. Cl.
*C07K 16/22*     (2006.01)
*A61K 39/395*    (2006.01)
*C07K 16/46*     (2006.01)
*A61K 39/00*     (2006.01)

(52) U.S. Cl.
CPC .......... *C07K 16/22* (2013.01); *A61K 39/3955* (2013.01); *C07K 16/468* (2013.01); *A61K 2039/505* (2013.01); *A61K 2039/507* (2013.01); *A61K 2039/545* (2013.01); *C07K 2317/31* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | |
|---|---|---|
| 5,500,362 A | 3/1996 | Robinson et al. |
| 5,821,337 A | 10/1998 | Carter et al. |
| 6,096,506 A | 8/2000 | Lee et al. |
| 6,368,597 B1 | 4/2002 | Strassmann et al. |
| 6,468,535 B1 | 10/2002 | Lee et al. |
| 6,858,208 B2 | 2/2005 | Lee et al. |
| 7,070,784 B1 | 7/2006 | Halkier et al. |
| 7,241,444 B2 | 7/2007 | Goetsch et al. |
| 7,261,893 B2 | 8/2007 | Veldman et al. |
| 7,320,789 B2 | 1/2008 | Aghajanian et al. |
| 7,534,432 B2 | 5/2009 | Lee et al. |
| 7,632,499 B2 | 12/2009 | Davies et al. |
| 7,635,760 B2 | 12/2009 | Han et al. |
| 7,655,763 B2 | 2/2010 | Veldman et al. |
| 7,731,961 B1 | 6/2010 | Aghajanian et al. |
| 7,745,583 B2 | 6/2010 | Han et al. |
| 7,785,587 B2 | 8/2010 | Whittemore et al. |
| 7,807,159 B2 | 10/2010 | Chin et al. |
| 7,807,631 B2 | 10/2010 | Knopf et al. |
| 7,888,486 B2 | 2/2011 | Walsh et al. |
| 7,892,561 B2 | 2/2011 | Junker et al. |
| 7,910,107 B2 | 3/2011 | Walsh et al. |
| 8,309,082 B2 | 11/2012 | Han et al. |
| 8,586,713 B2 | 11/2013 | Davis et al. |

(Continued)

FOREIGN PATENT DOCUMENTS

| | | |
|---|---|---|
| EP | 2594280 | 5/2013 |
| WO | 2004/037861 A2 | 5/2004 |

(Continued)

OTHER PUBLICATIONS

Paul, Fundamental Immunology, 1993, Raven Press, New York, pp. 292-295.*
Casset et al. (Biochem Biophys Res Comm. 2003; 307:198-205).*
MacCallunn et al. (J Mol Biol. 1996; 262:732-745).*
Vajdos et al. (J Mol Biol. 2002; 320(2):415-428).*
Holm et al. (Mol Innnnunol. 2007; 44(6):1075-1084).*
Chen et al. (J Mol Biol. 1999; 293:865-881).*
Al-Lazikani et al., "Standard Conformations for the Canonical Structures of Immunoglobulins"; J Mol Biol; 273(4):927-948 (1997).

(Continued)

*Primary Examiner* — Elizabeth C. Kemmerer
(74) *Attorney, Agent, or Firm* — Merchant & Gould, P.C.

(57) ABSTRACT

The present invention provides compositions and methods which involve specifically antagonizing GDF8 and Activin A. In certain embodiments, compositions are provided which comprise a GDF8-specific binding protein and an Activin A-specific binding protein. For example, the invention includes compositions comprising an anti-GDF8 antibody and an anti-Activin A antibody. In other embodiments, antigen-binding molecules are provided which comprise a GDF8-specific binding domain and an Activin A-specific binding domain. For example, the invention includes bispecific antibodies that bind GDF8 and Activin A. The compositions of the present invention are useful for the treatment of diseases and conditions characterized by reduced muscle mass or strength, as well as other conditions which are treatable by antagonizing GDF8 and/or Activin A activity.

18 Claims, No Drawings

Specification includes a Sequence Listing.

(56) References Cited

U.S. PATENT DOCUMENTS

| | | | |
|---|---|---|---|
| 8,840,894 B2 | 9/2014 | Stitt et al. | |
| 8,871,209 B2 * | 10/2014 | Stitt | A61K 39/3955 424/158.1 |
| 9,260,515 B2 | 2/2016 | Stitt et al. | |
| 2004/0142382 A1 | 7/2004 | Veldman et al. | |
| 2005/0175612 A1 | 8/2005 | Lee et al. | |
| 2006/0034831 A1 | 2/2006 | Tobin | |
| 2007/0178095 A1 | 8/2007 | Smith et al. | |
| 2007/0280945 A1 | 12/2007 | Stevens et al. | |
| 2008/0187543 A1 | 8/2008 | Kambadur et al. | |
| 2008/0299126 A1 | 12/2008 | Han et al. | |
| 2009/0136481 A1 | 5/2009 | Kambadur et al. | |
| 2009/0148436 A1 | 6/2009 | Lavallie et al. | |
| 2009/0227497 A1 | 9/2009 | Sun et al. | |
| 2009/0311252 A1 | 12/2009 | Knopf et al. | |
| 2010/0080811 A1 | 4/2010 | Davies et al. | |
| 2010/0166764 A1 | 7/2010 | Sayers et al. | |
| 2010/0272734 A1 | 10/2010 | Berger et al. | |
| 2010/0322942 A1 | 12/2010 | Whittemore et al. | |
| 2011/0008375 A1 | 1/2011 | Hq et al. | |
| 2011/0020330 A1 | 1/2011 | Aghajanian et al. | |
| 2011/0256132 A1 | 10/2011 | Ashman et al. | |
| 2011/0293630 A1 | 12/2011 | Stitt et al. | |
| 2012/0015877 A1 | 1/2012 | Seehra et al. | |
| 2012/0237521 A1 | 9/2012 | Berger et al. | |
| 2013/0336982 A1 | 12/2013 | Mader et al. | |
| 2015/0037339 A1 | 2/2015 | Gromada et al. | |
| 2016/0304595 A1 | 10/2016 | Pordy et al. | |
| 2016/0340421 A1 | 11/2016 | Stitt et al. | |

FOREIGN PATENT DOCUMENTS

| | | |
|---|---|---|
| WO | 2005/094446 A2 | 10/2005 |
| WO | 2005/103081 A2 | 11/2005 |
| WO | 2006/116269 A2 | 11/2006 |
| WO | 2007/044411 A2 | 4/2007 |
| WO | 2007/047112 A2 | 4/2007 |
| WO | 2008/031061 A2 | 3/2008 |
| WO | 2009/059943 A1 | 5/2009 |
| WO | 2009058346 A1 | 5/2009 |
| WO | 2010/070094 A1 | 6/2010 |
| WO | 2011/063018 A1 | 5/2011 |
| WO | 2011/150008 A1 | 12/2011 |
| WO | 2012/064771 A1 | 5/2012 |
| WO | 2013/074557 A1 | 5/2013 |
| WO | 2015/022658 | 2/2015 |

OTHER PUBLICATIONS

Altschul et al., "Basic local alignment search tool"; J Mol Biol; 215(3):403-410 (1990).

Altschul et al., "Gapped BLAST and PSI-BLAST: a new generation of protein database search programs"; Nucleic Acids Res; 25(17):3389-3402 (1997).

Angal et al., "A single amino acid substitution abolishes the heterogeneity of chimeric mouse/human (IgG4) antibody"; Molecular Immunology; 30(1):105-108 (Jan. 1993).

Brown et al., "Tolerance of single, but Not Multiple, Amino Acid Replacements in Antibody $V_H$ CDR2: A Means of Minimizing B Cell Wastage from Somatic Hypermutation?"; The J of Immunology; 156(9):3285-3291 (May 1, 1996).

Canziani et al., "Characterization of neutralizing affinity-matured human respiratory syncytial virus F binding antibodies in the sub-picomolar affinity range"; J of Molecular Recognition; 25(3):136-146 (Mar. 28, 2012).

Chilean Substantive Report dated Oct. 10, 2014, in corresponding Chilean Patent Application 3283-2012.

Clynes et al., "Fc receptors are required in passive and active immunity to melanoma"; Immunology, Proc. Nat'l. Acad. Sci. USA; 95:652-656 (Jan. 1998).

Cochrane et al., "Renal Structural and Functional Repair in a Mouse Model of Reversal of Ureteral Obstruction"; J Am Soc Nephrol; 16(12):3623-3630 (Dec. 1, 2005).

Columbian Office Action dated Aug. 19, 2014 for related Columbian patent application 12233131.

Davies et al., "Affinity improvement of single antibody VH domains: residues in all three hypervariable regions affect antigen binding" Immunotechnology, 2(3):169-179 (Sep. 1996).

Dufner et al., "Harnessing phage and ribosome display for antibody optimisation"; Trends in Biotechnology; 24(11):523-529 (Nov. 1, 2006).

Ehring, "Hydrogen Exchange/electrospray Ionizatino Mass Spectrometry Sudies of Structural Features of Proteins and Protein/Protein Interactions"; Analytical Biochemistry; 267(2):252-259 (Feb. 15, 1999).

Engen et al., "Investigating protein structure and dynamics by hydrogen exchange MS"; Anal. Chem.; 73(9):256A-265A (May 1, 2001).

Giusti et al., "Somatic diversification of S107 from an antiphosphocholine to an anti-DNA autoantibody is due to a single base change in its heavy chain variable region"; PNAS, USA, 84(9):2926-2930 (May 1987).

Gonnet et al., "Exhaustive Matching of the Entire Protein Sequence Database"; Science; 256(5062):1443-1445 (Jun. 5, 1992).

Goodson, "Dental applications"; Medical Applications of Controlled Release; 2:115-138 (1984).

Hanes et al., "Picomolar Affinity Antibodies from a Fully Synthetic Naïve Library Selected and Evolved by Ribosome Display"; Nature Biotechnology; 18(12):1287-1292 (Dec. 1, 2000).

Holt et al., "Domain antibodies: proteins for therapy"; Trends in Biotechnology; 21(11):484-490 (Nov. 2003).

Hoogenboom, "Selecting and screening recombinant antibody libraries"; Nature Biotechnology; 23(9):1105-1116 (Sep. 1, 2005).

International Search Report dated May 23, 2013, in corresponding PCT/US2012/064911.

International Search Report dated Sep. 21, 2011, in corresponding PCT/US2011/037837.

International Search Report dated Jan. 8, 2015, in PCT/US2014/048957.

Junghans et al., "Anti-Tac-H, a Humanized Antibody to the Interleukin 2 Receptor with New Features for Immunotherapy in Malignant and Immune Disorders"; Cancer Res.; 50:1495-1502 (Mar. 1, 1990).

Kabat, "Sequences of Proteins of Immunological Interest"; National Institutes of Health (U.S.); 6 pages. (1991).

Kazane et al., "Self-Assembled Antibody Multimers through Peptide Nucleic Acid Conjugation"; J Am Chem Soc.; 135(1):340-346 (Jan. 9, 2013).

Khurana et al., "Pharmacological Strategies for Muscular Dystrophy"; Nature Reviews/Druq Discovery; 2.379-390 (2003).

Klein et al., "Progress in overcoming the chain association issuein bispecific heterodimeric IgG antibodies"; mAbs 4(6):653-663 (Nov./Dec. 2012).

Kufer et al.; "A revival of bispecific antibodies"; Trends Biotechnol; 22(5):238-244 (May 2004).

Kussie et al., "A Single Engineered Amino Acid Substitution Changes Antibody Fine Specificity"; J of Immunology; 152:146-152 (1994).

Langer, "New Methods of Drug Delivery"; Science; 249:1527-1533 (Sep. 23, 1990).

Lee et al., "Regulation of GDF-11 and myostatin activity by GASP-1 and GASP-2"; PNAS USA.; 110(3):E3713-E3722 (Sep. 9, 2013).

Liu et al., "Fine mapping of the antigen-antibody interaction of scFv215, a recombinant antibody inhibiting RNA polymerase II from Drosophila melanogaster"; J of Molecular Recognition; 12(2):103-111 (1999).

MacCallum et al., "Antibody-Antigen Interactions: Contact Analysis and Binding Site Topography"; J. Mol. Biol.; 262(5):732-745 (Oct. 11, 1996).

Martin et al., "Modeling antibody bypervariable loops: A combined algorithm"; PNAS USA; 86(23):9268-9272 (Dec. 1, 1989).

Maynard et al., "Antibody Engineering"; Annu. Rev. Biomed. Eng.; 02:339-376 (2000).

(56) References Cited

OTHER PUBLICATIONS

McPherron et al., "Regulation of skeletal muscle mass in mice by a new TGF-β superfamily member"; Nature; 387(6628):83-90 (May 1, 1997).
Mordenti et al., "Interspecies Scaling of Clearance and Volume of Distribution Data for Five Therapeutic Proteins"; Pharm Res; 8(11):1351-1359 (Nov. 1991).
Munoz et al., "Biologicals Targeting Myostatin/GDF-11/Activins Prevent Burn-Induced Muscle Loss in Mice"; Journal of Surgical Research; 186(2)(abstract 34.6):591-592 (Feb. 2014).
Orcutt et al., "Engineering an antibody with picomolar affinity to DOTA chelates of multiple radionuclides for pretargeted radioimmunotherapy and imaging"; Nuclear Medicin and Biology; 38(2):223-233 (Aug. 31, 2010).
Pearson, "Using the FASTA program to search protein and DNA sequence databases"; Methods Mol Biol,; 24(Ch 26): 307-331 (1994).
Pearson, "Flexible sequence similarity searching with the FASTA3 program package", Methods Mol Biol 132: 185-219 (2000).
Pini et al., "Design and Use of a Phage Display Library: Human Antibodies with Subnanomolar Affinity Against a Marker of Angiogenesis Eluted from a Two-Dimentional Gel", The Journal of Biological Chemistry, 273(34):21769-21776 (Aug. 21, 1998).
Powell et al., "Compendium of Excipients for Parenteral Formulations"; J of Pharm Science & Technology; 52(5):238-311 (Sep.-Oct. 1998).
Rajpal et al., "A general method for greatly improving the affinity of antibodies by using combinatorial libraries"; Proceedings of the Nat'l Acad of Sci US; 102(24)8466-8471 (Jun. 1, 2005).
Reddy et al., "Elimination of Fc Receptor-Dependent Effector Functions of a Modified IgG4 Monoclonal Antibody to Human CD4"; J Immunol; 164:1925-1933 (2000).
Reineke, "Antibody epitope mapping using arrays of synthetic peptides"; Methods Mol Biol; 248(26):443-463 (2004).
Rudikoff et al., "Single amino acid substitution altering antigen-binding specificity". PNAS, USA, 79:1979-1983, (Mar. 1982).
Schildbach, et al., Heavy Chain Position 50 Is a Determinant of Affinity and Specificity for the Anti-digoxin Antibody 26-10'. The J of Biological Chemistry, 268(29):21739-21747 (Oct. 15, 1993).
Schildbach et al., "Contribution of a single heavy chain residue to specificity of an anti-digoxin monoclonal antibody", Protein Science, 3(5):737-749 (1994).
Sefton, "Implantable Pumps"; CRC Crit. Ref. Biomed. Eng. 14:201-240 (1987).
Shield et al., "Lack of fucose on human IgG1 N-linked oligosaccharide improves binding to human Fcgamma RIII and antibody-dependent cellular toxicity"; J Biol Chem; 277(30)26733-26740 (Jul. 2002).
Souza et al., "Proteomic identification and functional validation of activins and bone morphogenetic protein 11 as candidate novel muscle mass regulators"; Mol Endocrinol; 22(12):2689-2702 (Dec. 22, 2008).
Sozzani et al., "The yin and yang of Activin A"; Blood; 117(19):5013-5015 (May 12, 2011).
Sutcliffe et al. , "Antibodies that React with Predetermined Sites on Proteins"; Science; 219:660-666 (Feb. 11, 1983).
Taylor et al., "A Transgenic Mouse that Expresses a Diversity of Human Sequence Heavy and Light Chain Immunoglobulins"; Nucleic Acids Research; 20{23):6287-6295 (1992).
Tomer, Hochleitner et al., "Characterization of a discontinuous epitope of the human immunodeficiency virus (HIV) core protein p24 by epitope excision and differential chemical modification followed by mass spectrometric peptide mapping analysis"; Protein Sci; 9:487-496 (2000).
Tornetta et al., "Antibody Fab display and selection through fusion to the pIX coat protein of filamentous phage"; J. Immunological Methods; 360(1-2):39-46 (Aug. 31, 2010).
Tsuchida et al., "Activin signaling as an emerging target for therapeutic interventions"; Cell Commun Signal; 7:15 (Jun. 18, 2009).
Tutt et al., "Trispecific F(ab')3 derivatives that use cooperative signaling via the TCR/CD3 complex and CD2 to activate and redirect resting cytotoxic T cells"; J Immunol; 147(1):60-69 (1991).
Vajdos et al., "Comprehensive Functional Maps of the Antigen-Binding Site of an Anti-ErbB2 Antibody Obtained with Shotgun Scanning Mutagenesis"; J. Mol. Biol. 320{2):415-428 (Jul. 2002).
Wark et al., "Lates technologies for the enhancement of antibody affinity"; Advanced Drug Delivery Reviews; 58(5-6):657-670 (Aug. 7, 2006).
Whittemore et al., "Inhibition of myostatin in adult mice increases skeletal muscle mass and strength"; Biochem, Biophys. Res. Commun 300:965-971 (2003).
Wu et al., "Receptor-Mediated in Vitro Gene Transformation by a Soluble DNA Carrier System"; Journal of Biological Chemistry; 262(10):4429-4432 (1987).
Wu et al., "Humanization of a Murine Monoclonal Antibody by Simultaneous Optimization of Framework and CDR Residues", J. Mol. Biol.; 294(1): 151-162 (Nov. 19, 1999).
Xiang et al., "Study of B72.3 combining sites by molecular modeling and site-directed mutagenesis", Protein Eng. 13(5):339-344 (May 2000).
Abbott et al., "Current approaches to fine mapping of antigen-antibody interactions," Immunology.; 142(4):526-535 (Aug. 2014).
Allen et al., "Expression and function of myostatin in obesity, diabetes, and exercise adaptation," Medicine and Science in Sports and Exercise, vol. 43, No. 10, pp. 1828-1835 (Oct. 1, 2011).
Bogdanovich et al., "Myostatin blockade improves function but not histopathology in a murine model of limb-girdle muscular dystrophy 2C," Muscle Nerve, Mar. 2008, vol. 37, pp. 308-316.
Boder et al., "directed evolution of antibody fragments with monovalent femtomolar antigen-binding affinity," Proc Natl Acad SCi USA.; 97(20):10701-10705 (Sep. 26, 2000).
Cadena et al., "Administration of a soluble activin type IIB receptor promotes muscle growth independent of fiber type," Journal of Applied Physiology, vol. 109, pp. 635-642 (2010).
Casset at al., "A peptide mimetic of an anti-CD4 monoclonal antibody by rational design," Biochemical and Biophysical Research Communications, 2003, vol. 307, pp. 198-205.
Chen et al., "Selection and analysis of an optimized anti-VEGF antibody: crystal structure of an affinity-matured Fab in complex with antigen," Journal of Molecular Biology, 1999, vol. 293, pp. 865-881.
Cook et al., Structural basis for a functional antagonist in the transforming growth factor beta superfamily. J Biol Chem.; 280(48): 40177-40186. (Epub Sep. 26, 2005) (Dec. 2, 2005).
He et al., "Activin A inhibits formation of skeletal muscle during chick development"; Anat. Embryol (Berl); 209(5):401-407 (Jun. 2005).
Holm et al., "Functional mapping and single chain construction of the anti-cytokeratin 8 monoclonal antibody TS1," Molecular Immunology, 2007, vol. 44, pp. 1075-1084.
Holzbaur et al., "Myostatin inhibition slows muscle atrophy in rodent models of amyotrophic lateral sclerosis," Nuerobiology of Disease, 2006, vol. 23, pp. 697-707.
International Search Report and Written Opinion dated Jun. 30, 2016 in PCT/US2016/027774, 22 pages total.
LeBrasseur et al., "Myostatin inhibition enhances the effects of exercise on performance and metabolic outcomes in aged mice," Journals of Gerontology, Series A, Biological Sciences and Medical Sciences, vol. 64A, No. 9, pp. 940-948 (2009).
Lee et al., "Regulation of muscle growth by multiple ligands signaling through Activin type II receptors"; PNAS USA; 102(50):18117-18122 (Dec. 13, 2005) (Epub Dec. 5, 2005).
Lee et al., "Extracellular regulation of myostatin: a molecular rheostat for muscle mass," Immunol Endocr Metab Agents Med Chem, 2010, vol. 10, pp. 183-194.
Lin et al., "The structural basis of TGF-beta, bone morphogenetic protein, and activing ligand binding." Reproduction. 132(2): 179-190 (Aug. 2006).
McPherron et al., "Redundancy of myostatin and growth/differentiation factor 11 function"; BMC Dev Biol; 9:24 (9 pgs) (Mar. 19, 2009).

(56) References Cited

OTHER PUBLICATIONS

McPherron, "Metabolic functions of myostatin and GDF11," Immunol Endocr Metab Agents Med Chem, Dec. 2010, 10(4):217-231.

Musculoskeletal Diseases, in MESH Database, National Center for Biotechnology Information, Bethesda, Maryland, USA [online], [retrieved on Jan. 9, 2017]. Retrieved from the Internet: <URL: https://www.ncbi.nlm.nih.gov/mesh/?term=musculoskeletal=diseases>. 4 pages total.

Padhi et al., Pharmacological inhibition of myostatin and changes in lean body mass and lower extremity muscle size in patients receiving androgen deprivation therapy for prostate cancer, Journal of Clinical Endocrinology and Metabolism, vol. 99, No. 10, pp. E1967-E1975 (Oct. 2014).

Pascalis et al., "Grafting of "abbreviated" complentarity-determining regions containing specificity-determining residues essential for ligand contact to engineer a less immunogenic humanized monoclonal antibody", Journal of Immunology, 2002, vol. 169, pp. 30763084.

Sharp et al., "The effects of a myostatin inhibitor on lean body mass, strength, and power in resistance trained males," Journal of the International Society of Sports Nutrition, vol. 11, No. Suppl 1, p. P42 (Dec. 1, 2014).

Singapore Search Report and Written Opinion dated Mar. 1, 2017 in corresponding application SG 11201600731W, 11 pages total.

Smith et al., "Myostatin inhibitors as therapies for muscle wasting associated with cancer and other and disorders," Current Opinion in Supportive and Palliative Care, vol. 7, No. 4, p. 352-360 (Dec. 2013).

Thompson et al., "Structures of an ActRIIB:activin A complex reveal a novel binding mode for TGF-beta ligand receptor interactions." EMBO J.; 22(7): 1555-1566 (Apr. 1, 2003).

Wagner et al., "A phase I/II trial of MYO-29 in adult subjects with muscular dystrophy," Annals of Neurology, vol. 63, No. 5, pp. 561-571 (May 1, 2008).

Willis et al., "Effects of aerobic and/or resistance training on body mass and fat mass in overweight or obese adults," Journal of Applied Physiology, 113(12): 1831-1837.

Xia et al., "The biology of activin: recent advances in structure, regulation, and function," J Endocrinol.; 202(1):1-12. (Jul. 2009) (Epub Mar. 9, 2009).

Zhou et al., "Reversal of cancer cachexia and muscle wasting by ActRIIB antagonism leads to prolonged survival," Cell, Aug. 20, 2010, vol. 142, pp. 531-543.

\* cited by examiner

```
                        SEQUENCE LISTING

<160> NUMBER OF SEQ ID NOS: 28

<210> SEQ ID NO 1
<211> LENGTH: 118
<212> TYPE: PRT
<213> ORGANISM: Artificial Sequence
<220> FEATURE:
<223> OTHER INFORMATION: Synthetic

<400> SEQUENCE: 1

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Ile His Trp Val Arg Gln Ala Pro Gly Lys Gly Leu Glu Trp Val
        35                  40                  45

Ala Val Ile Ser Tyr Asp Gly Ser Asp Glu Tyr Tyr Val Asp Ser Val
    50                  55                  60

Lys Gly Arg Phe Ser Ile Ser Arg Asp Asn Ser Lys Asn Thr Leu Tyr
65                  70                  75                  80

Leu Gln Met Asn Ser Leu Arg Pro Ala Asp Ser Ala Val Tyr Tyr Cys
                85                  90                  95

Val Lys Gly Asp Leu Glu Leu Gly Phe Asp Tyr Trp Gly Gln Gly Thr
                100                 105                 110

Leu Val Thr Val Ser Ser
        115

<210> SEQ ID NO 2
<211> LENGTH: 8
<212> TYPE: PRT
<213> ORGANISM: Artificial Sequence
<220> FEATURE:
<223> OTHER INFORMATION: Synthetic

<400> SEQUENCE: 2

Gly Phe Thr Phe Ser Arg Tyr Gly
```

```
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Ile Ser Tyr Asp Gly Ser Asp Glu
1               5

<210> SEQ ID NO 4
<211> LENGTH: 11
<212> TYPE: PRT
<213> ORGANISM: Artificial Sequence
<220> FEATURE:
<223> OTHER INFORMATION: Synthetic

<400> SEQUENCE: 4

Val Lys Gly Asp Leu Glu Leu Gly Phe Asp Tyr
1               5                   10

<210> SEQ ID NO 5
<211> LENGTH: 112
<212> TYPE: PRT
<213> ORGANISM: Artificial Sequence
<220> FEATURE:
<223> OTHER INFORMATION: Synthetic

<400> SEQUENCE: 5

Asp Ile Val Met Thr Gln Ala Ala Pro Ser Ile Pro Val Ile Pro Gly
1               5                   10                  15

Glu Ser Val Ser Met Ser Cys Arg Ser Ser Lys Ser Leu Leu Tyr Ser
            20                  25                  30

Asn Gly His Thr Tyr Val Tyr Trp Phe Val Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln Asn
                85                  90                  95

Leu Glu Phe Pro Leu Thr Phe Gly Ala Gly Thr Lys Leu Glu Leu Lys
            100                 105                 110

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Lys Ser Leu Leu Tyr Ser Asn Gly His Thr Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: Synthetic
```

<400> SEQUENCE: 7

Arg Met Ser
1

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

Met Gln Asn Leu Glu Phe Pro Leu Thr
1               5

<210> SEQ ID NO 9
<211> LENGTH: 120
<212> TYPE: PRT
<213> ORGANISM: Artificial Sequence
<220> FEATURE:
<223> OTHER INFORMATION: Synthetic

<400> SEQUENCE: 9

Glu Val Gln Val Leu Glu Ser Gly Gly Asp Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Thr Trp Val Arg Gln Ala Pro Gly Lys Gly Leu Glu Trp Val
        35                  40                  45

Ser Ala Ile Ser Gly Ser Gly Gly Ser Ala Tyr Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Asp Gly Ala Trp Lys Met Ser Gly Leu Asp Val Trp Gly Gln
            100                 105                 110

Gly Thr Thr Val Ile Val Ser Ser
        115                 120

<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Gly Phe Thr Phe Ser Ala Tyr Ala
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic

<400> SEQUENCE: 11

Ile Ser Gly Ser Gly Gly Ser Ala
1               5

<210> SEQ ID NO 12
<211> LENGTH: 13
<212> TYPE: PRT
<213> ORGANISM: Artificial Sequence
<220> FEATURE:
<223> OTHER INFORMATION: Synthetic

<400> SEQUENCE: 12

Ala Lys Asp Gly Ala Trp Lys Met Ser Gly Leu Asp Val
1               5                   10

<210> SEQ ID NO 13
<211> LENGTH: 107
<212> TYPE: PRT
<213> ORGANISM: Artificial Sequence
<220> FEATURE:
<223> OTHER INFORMATION: Synthetic

<400> SEQUENCE: 13

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Ala Trp Tyr Gln Gln Lys Pro Gly Lys Ile Pro Arg Leu Leu Ile
        35                  40                  45

Tyr Thr Thr Ser Thr Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Leu
                85                  90                  95

Thr Phe Gly Gly Gly Thr Lys Val Glu Ile Lys
            100                 105

<210> SEQ ID NO 14
<211> LENGTH: 6
<212> TYPE: PRT
<213> ORGANISM: Artificial Sequence
<220> FEATURE:
<223> OTHER INFORMATION: Synthetic

<400> SEQUENCE: 14

Gln Asp Ile Ser Asp Tyr
1               5

<210> SEQ ID NO 15
<211> LENGTH: 3
<212> TYPE: PRT
<213> ORGANISM: Artificial Sequence
<220> FEATURE:
<223> OTHER INFORMATION: Synthetic

<400> SEQUENCE: 15

Thr Thr Ser
1

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Gln Lys Tyr Asp Ser Ala Pro Leu Thr
1               5

<210> SEQ ID NO 17
<211> LENGTH: 121
<212> TYPE: PRT
<213> ORGANISM: Artificial Sequence
<220> FEATURE:
<223> OTHER INFORMATION: Synthetic

<400> SEQUENCE: 17

Gln Val Gln Leu Val Glu Ser Gly Gly Gly Val Val Gln Pro Gly Lys
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Val Ile Gly Tyr Asp Gly Gly Asn Glu Tyr Tyr Ala Asp Ser Val
    50                  55                  60

Lys Gly Arg Phe Thr Ile Ser Arg Asp Asn Ser Lys Asn Thr Leu Asn
65                  70                  75                  80

Leu Gln Met Ser Ser Leu Arg Ala Glu Asp Thr Ala Val Tyr Tyr Cys
                85                  90                  95

Ser Thr Ile Ser His Tyr Asp Ile Leu Ser Gly Met Asp Val Trp Gly
            100                 105                 110

Arg Gly Thr Thr Val Thr Val Ser Ser
        115                 120

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Gly Phe Thr Phe Ser Ser Phe Gly
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic

<400> SEQUENCE: 19

Ile Gly Tyr Asp Gly Gly Asn Glu
1               5

<210> SEQ ID NO 20
<211> LENGTH: 14
<212> TYPE: PRT
<213> ORGANISM: Artificial Sequence
<220> FEATURE:
<223> OTHER INFORMATION: Synthetic

<400> SEQUENCE: 20

Ser Thr Ile Ser His Tyr Asp Ile Leu Ser Gly Met Asp Val
1               5                   10

<210> SEQ ID NO 21

-continued

```
<211> LENGTH: 108
<212> TYPE: PRT
<213> ORGANISM: Artificial Sequence
<220> FEATURE:
<223> OTHER INFORMATION: Synthetic

<400> SEQUENCE: 21

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Ala Ser Gly Thr Asp Phe Thr Leu Thr Ile Asn Ser Leu Gln Pro
65                  70                  75                  80

Glu Asp Phe Ala Thr Tyr Tyr Cys Gln Gln Ala Asn Ser Phe Pro Leu
                85                  90                  95

Thr Phe Gly Gly Gly Thr Lys Val Glu Ile Lys Arg
            100                 105

<210> SEQ ID NO 22
<211> LENGTH: 6
<212> TYPE: PRT
<213> ORGANISM: Artificial Sequence
<220> FEATURE:
<223> OTHER INFORMATION: Synthetic

<400> SEQUENCE: 22

Gln Gly Ile Ser Asn Trp
1               5

<210> SEQ ID NO 23
<211> LENGTH: 3
<212> TYPE: PRT
<213> ORGANISM: Artificial Sequence
<220> FEATURE:
<223> OTHER INFORMATION: Synthetic

<400> SEQUENCE: 23

Ala Ala Ser
1

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Gln Gln Ala Asn Ser Phe Pro Leu Thr
1               5

<210> SEQ ID NO 25
<211> LENGTH: 109
<212> TYPE: PRT
<213> ORGANISM: Homo sapiens

<400> SEQUENCE: 25

Asp Phe Gly Leu Asp Cys Asp Glu His Ser Thr Glu Ser Arg Cys Cys
1               5                   10                  15
```

```
Arg Tyr Pro Leu Thr Val Asp Phe Glu Ala Phe Gly Trp Asp Trp Ile
                20                  25                  30

Ile Ala Pro Lys Arg Tyr Lys Ala Asn Tyr Cys Ser Gly Glu Cys Glu
            35                  40                  45

Phe Val Phe Leu Gln Lys Tyr Pro His Thr His Leu Val His Gln Ala
 50                  55                  60

Asn Pro Arg Gly Ser Ala Gly Pro Cys Cys Thr Pro Thr Lys Met Ser
 65                  70                  75                  80

Pro Ile Asn Met Leu Tyr Phe Asn Gly Lys Glu Gln Ile Ile Tyr Gly
                85                  90                  95

Lys Ile Pro Ala Met Val Val Asp Arg Cys Gly Cys Ser
            100                 105
```

<210> SEQ ID NO 26
<211> LENGTH: 426
<212> TYPE: PRT
<213> ORGANISM: Homo sapiens

<400> SEQUENCE: 26

```
Met Pro Leu Leu Trp Leu Arg Gly Phe Leu Leu Ala Ser Cys Trp Ile
 1               5                  10                  15

Ile Val Arg Ser Ser Pro Thr Pro Gly Ser Glu Gly His Ser Ala Ala
                20                  25                  30

Pro Asp Cys Pro Ser Cys Ala Leu Ala Ala Leu Pro Lys Asp Val Pro
            35                  40                  45

Asn Ser Gln Pro Glu Met Val Glu Ala Val Lys Lys His Ile Leu Asn
 50                  55                  60

Met Leu His Leu Lys Lys Arg Pro Asp Val Thr Gln Pro Val Pro Lys
 65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
            260                 265                 270

Gly Gly Gly Glu Gly Gly Ala Gly Ala Asp Glu Glu Lys Glu Gln Ser
        275                 280                 285
```

```
His Arg Pro Phe Leu Met Leu Gln Ala Arg Gln Ser Glu Asp His Pro
    290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                    325                 330                 335

Asp Trp Ile Ile Ala Pro Ser Gly Tyr His Ala Asn Tyr Cys Glu Gly
                340                 345                 350

Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
    370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
                420                 425

<210> SEQ ID NO 27
<211> LENGTH: 340
<212> TYPE: PRT
<213> ORGANISM: Artificial Sequence
<220> FEATURE:
<223> OTHER INFORMATION: Synthetic

<400> SEQUENCE: 27

Glu Ala Glu Thr Arg Glu Cys Ile Tyr Tyr Asn Ala Asn Trp Glu Leu
1               5                   10                  15

Glu Arg Thr Asn Gln Ser Gly Leu Glu Arg Cys Glu Gly Glu Gln Asp
                20                  25                  30

Lys Arg Leu His Cys Tyr Ala Ser Trp Ala Asn Ser Ser Gly Thr Ile
            35                  40                  45

Glu Leu Val Lys Lys Gly Cys Trp Leu Asp Asp Phe Asn Cys Tyr Asp
50                  55                  60

Arg Gln Glu Cys Val Ala Thr Glu Glu Asn Pro Gln Val Tyr Phe Cys
65                  70                  75                  80

Cys Cys Glu Gly Asn Phe Cys Asn Glu Arg Phe Thr His Leu Pro Glu
                85                  90                  95

Ala Gly Gly Pro Glu Val Thr Tyr Glu Pro Pro Thr Ala Pro Ser
                100                 105                 110

Gly Asp Lys Thr His Thr Cys Pro Pro Cys Pro Ala Pro Glu Leu Leu
            115                 120                 125

Gly Gly Pro Ser Val Phe Leu Phe Pro Pro Lys Pro Lys Asp Thr Leu
        130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
        195                 200                 205

Gly Lys Glu Tyr Lys Cys Lys Val Ser Asn Lys Ala Leu Pro Ala Pro
    210                 215                 220
```

Ile Glu Lys Thr Ile Ser Lys Ala Lys Gly Gln Pro Arg Glu Pro Gln
225                 230                 235                 240

Val Tyr Thr Leu Pro Pro Ser Arg Asp Glu Leu Thr Lys Asn Gln Val
                245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
        275                 280                 285

Pro Val Leu Asp Ser Asp Gly Ser Phe Phe Leu Tyr Ser Lys Leu Thr
    290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly Lys
            340

<210> SEQ ID NO 28
<211> LENGTH: 407
<212> TYPE: PRT
<213> ORGANISM: Homo Sapiens

<400> SEQUENCE: 28

Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Ser Pro Thr Pro
            20                  25                  30

Pro Pro Thr Pro Ala Ala Gln Pro Pro Pro Pro Pro Gly Ser Pro
        35                  40                  45

Gly Gly Ser Gln Asp Thr Cys Thr Ser Cys Gly Gly Phe Arg Arg Pro
    50                  55                  60

Glu Glu Leu Gly Arg Val Asp Gly Asp Phe Leu Glu Ala Val Lys Arg
65                  70                  75                  80

His Ile Leu Ser Arg Leu Gln Met Arg Gly Arg Pro Asn Ile Thr His
                85                  90                  95

Ala Val Pro Lys Ala Ala Met Val Thr Ala Leu Arg Lys Leu His Ala
            100                 105                 110

Gly Lys Val Arg Glu Asp Gly Arg Val Glu Ile Pro His Leu Asp Gly
        115                 120                 125

His Ala Ser Pro Gly Ala Asp Gly Gln Glu Arg Val Ser Glu Ile Ile
    130                 135                 140

Ser Phe Ala Glu Thr Asp Gly Leu Ala Ser Ser Arg Val Arg Leu Tyr
145                 150                 155                 160

Phe Phe Ile Ser Asn Glu Gly Asn Gln Asn Leu Phe Val Val Gln Ala
                165                 170                 175

Ser Leu Trp Leu Tyr Leu Lys Leu Leu Pro Tyr Val Leu Glu Lys Gly
            180                 185                 190

Ser Arg Arg Lys Val Arg Val Lys Val Tyr Phe Gln Glu Gln Gly His
        195                 200                 205

Gly Asp Arg Trp Asn Met Val Glu Lys Arg Val Asp Leu Lys Arg Ser
    210                 215                 220

Gly Trp His Thr Phe Pro Leu Thr Glu Ala Ile Gln Ala Leu Phe Glu
225                 230                 235                 240

Arg Gly Glu Arg Arg Leu Asn Leu Asp Val Gln Cys Asp Ser Cys Gln

-continued

```
                245                 250                 255
Glu Leu Ala Val Val Pro Val Phe Val Asp Pro Gly Glu Glu Ser His
            260                 265                 270

Arg Pro Phe Val Val Val Gln Ala Arg Leu Gly Asp Ser Arg His Arg
        275                 280                 285

Ile Arg Lys Arg Gly Leu Glu Cys Asp Gly Arg Thr Asn Leu Cys Cys
    290                 295                 300

Arg Gln Gln Phe Phe Ile Asp Phe Arg Leu Ile Gly Trp Asn Asp Trp
305                 310                 315                 320

Ile Ile Ala Pro Thr Ser Tyr Tyr Gly Asn Tyr Cys Glu Gly Ser Cys
            325                 330                 335

Pro Ala Tyr Leu Ala Gly Val Pro Gly Ser Ala Ser Ser Phe His Thr
            340                 345                 350

Ala Val Val Asn Gln Tyr Arg Met Arg Gly Leu Asn Pro Gly Thr Val
            355                 360                 365

Asn Ser Cys Cys Ile Pro Thr Lys Leu Ser Thr Met Ser Met Leu Tyr
        370                 375                 380

Phe Asp Asp Glu Tyr Asn Ile Val Lys Arg Asp Val Pro Asn Met Ile
385                 390                 395                 400

Val Glu Glu Cys Gly Cys Ala
                405
```

COMPOSITIONS AND METHODS FOR INCREASING MUSCLE MASS AND MUSCLE STRENGTH BY SPECIFICALLY ANTAGONIZING GDF8 AND OR ACTIVIN A

CROSS-REFERENCE TO RELATED APPLICATIONS

This application is a continuation application of U.S. application Ser. No. 15/282,489, filed on Sep. 30, 2016, now abandoned, which is a continuation application of U.S. application Ser. No. 15/077,662, filed Mar. 22, 2016, now abandoned, which is a continuation application of U.S. application Ser. No. 14/496,941, filed Sep. 25, 2014, now abandoned, which is a continuation application of U.S. application Ser. No. 13/676,233 filed Nov. 14, 2012, now issued as U.S. Pat. No. 8,871,209, which claims the benefit under 35 U.S.C. § 119(e) of U.S. provisional application No. 61/559,175, filed on Nov. 14, 2011; 61/607,024, filed on Mar. 6, 2012; and 61/661,451, filed on Jun. 19, 2012, the disclosures of each of which are herein incorporated by reference in their entireties.

FIELD OF THE INVENTION

The present invention relates to compositions and methods for increasing muscle mass and muscle strength in a subject. More specifically, the invention relates to compositions that specifically bind GDF8 and Activin A and the use of such compositions to treat diseases and disorders characterized by decreased muscle mass or strength.

BACKGROUND

Growth and differentiation factor-8 (GDF8, also known as myostatin), is a secreted ligand belonging to the transforming growth factor-β (TGF-β) superfamily of growth factors. GDF8 plays a central role in the development and maintenance of skeletal muscle, acting as a negative regulator of muscle mass. While the myostatin null mouse phenotype demonstrates the importance of GDF8 in the control of muscle size during development, muscle hypertrophy can also be elicited in adult muscle through inhibition of GDF8 with neutralizing antibodies, decoy receptors, or other antagonists. Administration of GDF8 neutralizing antibodies has been reported to result in muscle mass increases of between 10 and 30%. The increased muscle mass seen is due to increased fiber diameter as opposed to myofiber hyperplasia (fiber number). A number of studies have also reported increases in muscle strength or performance commensurate with increased size including twitch and tetanic force. Use of a cleavage resistant version of the GDF8 propeptide also leads to increased muscle size.

Other GDF8 antagonists have been used in adult mice with significant effects on skeletal muscle mass. These include the extracellular portion of the Type II GDF8 receptor, ActRIIB, stabilized by fusion to an IgG Fc domain ("ActRIIB-Fc"). The clinical molecule "ACE-031" is an example of an ActRIIB-Fc molecule.

Although ActRIIB-Fc has been shown to increase muscle mass in experimental animals, in human clinical trials this molecule was shown to cause various adverse side effects. For example, administration of ACE-031 to postmenopausal women in a Phase Ib ascending dose study was shown to cause undesired increases in hemoglobin and decreases in FSH levels. In addition, a Phase II study of ACE-031 in pediatric patients with muscular dystrophy was discontinued due to adverse effects including nose and gum bleeding. Dilated blood vessels are also observed in patients treated with ActRIIB-Fc.

Experiments have shown that the muscle growth-inducing effects of ActRIIB-Fc are attenuated but not eliminated in myostatin null mice, suggesting that ActRIIB-Fc exerts its muscle mass-inducing effects by antagonizing other ActRIIB ligand(s) in addition to GDF8. Other ligands that bind ActRIIB include Activin A, Activin B, Activin AB, Inhibin A, Inhibin B, GDF3, GDF11, Nodal, BMP2, BMP4, and BMP7.

BRIEF SUMMARY OF THE INVENTION

The present inventors hypothesized that the enhanced muscle growth effects of ActRIIB-Fc, as well as its unwanted side effects, are due to the binding of this molecule to additional ligands beside GDF8. Thus, the inventors sought to determine if it was possible to specifically antagonize only certain ActRIIB ligands but not others in order to produce the enhanced muscle growth effects of ActRIIB-Fc while at the same time avoiding the unwanted adverse side effects associated with this molecule. Through the experimentation set out in the Examples herein, it was surprisingly discovered that significant muscle growth enhancement could be achieved by specifically antagonizing Activin A. Importantly, it was also determined that the desired therapeutic effects of ActRIIB-Fc (e.g., enhanced skeletal muscle growth) could be achieved without unwanted side effects by specifically antagonizing GDF8 and Activin A but not antagonizing other ActRIIB ligands (e.g., GDF11, BMP9, BMP10, etc.).

Thus, according to one aspect of the present invention, a composition is provided comprising a GDF8-specific binding protein and an Activin A-specific binding protein. In certain embodiments, the GDF8-specific binding protein is an anti-GDF8 antibody and/or the Activin A-specific binding protein is an anti-Activin A antibody. According to a related aspect of the invention, an antigen-binding molecule is provided comprising a GDF8-specific binding domain and an Activin A-specific binding domain. In one embodiment of this aspect of the invention, the antigen-binding molecule is a bispecific antibody comprising a first variable domain that specifically binds GDF8 and a second variable domain that specifically binds Activin A.

The present invention provides methods for increasing muscle mass or strength in a subject by administering to the subject an Activin A-specific binding protein. The present invention also provides methods for increasing muscle mass or strength in a subject by administering to the subject a GDF8-specific binding protein and an Activin A-specific binding protein, or by administering to the subject an antigen-binding molecule comprising a GDF8-specific binding domain and an Activin A-specific binding domain. The methods according to this aspect of the invention are useful for treating diseases or disorders associated with decreased muscle mass, strength or power, including, e.g., cachexia, sarcopenia and other muscle-wasting conditions.

Other embodiments of the present invention will become apparent from a review of the ensuing detailed description.

DETAILED DESCRIPTION

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Antigen-Specific Binding Proteins

The present invention relates to compositions comprising antigen-specific binding proteins. More specifically, the present invention provides a composition comprising a GDF8-specific binding protein and an Activin A-specific binding protein.

As used herein, the expression "antigen-specific binding protein" means a protein comprising at least one domain which specifically binds a particular antigen. Exemplary categories of antigen-specific binding proteins include antibodies, antigen-binding portions of antibodies, peptides that specifically interact with a particular antigen (e.g., peptibodies), receptor molecules that specifically interact with a particular antigen, and proteins comprising a ligand-binding portion of a receptor that specifically binds a particular antigen.

The present invention includes antigen-specific binding proteins that specifically bind GDF8, "GDF8-specific binding proteins". The term "GDF8" (also referred to as "growth and differentiation factor-8" and "myostatin") means the protein having the amino acid sequence of SEQ ID NO:25 (mature protein). According to the present invention, GDF8-specific binding proteins specifically bind GDF8 but do not bind other ActRIIB ligands such as GDF3, BMP2, BMP4, BMP7, BMP9, BMP10, GDF11, Activin A, Activin B, Activin AB, Nodal, etc.

The present invention also includes antigen-specific binding proteins that specifically bind Activin A, i.e., "Activin A-specific binding proteins". Activins are homo- and heterodimeric molecules comprising βA and/or βB subunits. The βA subunit has the amino acid sequence of SEQ ID NO:26 and the βB subunit has the amino acid sequence of SEQ ID NO:28. Activin A is a homodimer of two βA subunits; Activin B is a homodimer of two βB subunits; and Activin AB is a heterodimer of one βA subunit and one βB subunit. An Activin A-specific binding protein may be an antigen-specific binding protein that specifically binds the βA subunit. Since the βA subunit is found in both Activin A and Activin AB molecules, an "Activin A-specific binding protein" can be an antigen-specific binding protein that specifically binds Activin A as well as Activin AB (by virtue of its interaction with the βA subunit). Therefore, according to the present invention, an Activin A-specific binding protein specifically binds Activin A, or Activin A and Activin AB, but does not bind other ActRIIB ligands such as Activin B, GDF3, GDF8, BMP2, BMP4, BMP7, BMP9, BMP10, GDF11, Nodal, etc.

In the context of the present invention, molecules such as ActRIIB-Fc (e.g., "ACE-031"), which comprise the ligand-binding portion of the ActRIIB receptor, are not considered "GDF8-specific binding proteins" or "Activin A-specific binding proteins" because such molecules bind multiple ligands besides GDF8, Activin A and Activin AB.

Antigen-Binding Molecules with Two Different Antigen-Specific Binding Domains

The present invention also includes antigen-binding molecules comprising two different antigen-specific binding domains. In particular, the present invention includes antigen-binding molecules comprising a GDF8-specific binding domain and an Activin A-specific binding domain. The term "antigen-specific binding domain," as used herein, includes polypeptides comprising or consisting of: (i) an antigen-binding fragment of an antibody molecule, (ii) a peptide that specifically interacts with a particular antigen (e.g., a peptibody), and/or (iii) a ligand-binding portion of a receptor that specifically binds a particular antigen. For example, the present invention includes bispecific antibodies with one arm comprising a first heavy chain variable region/light chain variable region (HCVR/LCVR) pair that specifically binds GDF8 and another arm comprising a second HCVR/LCVR pair that specifically binds Activin A.

Specific Binding

The term "specifically binds" or the like, as used herein, means that an antigen-specific binding protein, or an antigen-specific binding domain, forms a complex with a particular antigen characterized by a dissociation constant ($K_D$) of 500 pM or less, and does not bind other unrelated antigens under ordinary test conditions. "Unrelated antigens" are proteins, peptides or polypeptides that have less than 95% amino acid identity to one another. Methods for determining whether two molecules specifically bind one another are well known in the art and include, for example, equilibrium dialysis, surface plasmon resonance, and the like. For example, an antigen-specific binding protein or an antigen-specific binding domain, as used in the context of the present invention, includes molecules that bind a particular antigen (e.g., GDF8, or Activin A and/or AB) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

As used herein, an antigen-specific binding protein or antigen-specific binding domain "does not bind" to a specified molecule (e.g., "does not bind GDF11", "does not bind BMP9", "does not bind BMP10", etc.) if the protein or binding domain, when tested for binding to the molecule at 25° C. in a surface plasmon resonance assay, exhibits a $K_D$ of greater than 1000 pM, or fails to exhibit any binding in such an assay or equivalent thereof.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C.

Antibodies and Antigen-Binding Fragments of Antibodies

As indicated above, an antigen-specific binding protein can comprise or consist of an antibody or antigen-binding fragment of an antibody. Furthermore, in the case of antigen-binding molecules comprising two different antigen-specific binding domains, one or both of the antigen-specific binding domains may comprise or consist of an antigen-binding fragment of an antibody.

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the antibodies of the invention (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; $V_H$-$C_H2$-$C_H3$; (vii) $V_H$-$C_L$; $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

The molecules of the present invention may comprise or consist of human antibodies and/or recombinant human antibodies, or fragments thereof. The term "human antibody", as used herein, includes antibodies having variable and constant regions derived from human germline immunoglobulin sequences. Human antibodies may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The molecules of the present invention may comprise or consist of recombinant human antibodies or antigen-binding fragments thereof. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Anti-GDF8 Antibodies and Antigen-Binding Fragments Thereof

In certain specific embodiments of the present invention, the GDF8-specific binding protein, or the GDF8-specific binding domain, comprises or consists of an anti-GDF8 antibody or antigen-binding fragment thereof. Anti-GDF8 antibodies are mentioned in, e.g., U.S. Pat. Nos. 6,096,506; 7,320,789; 7,261,893; 7,807,159; 7,888,486; 7,635,760; 7,632,499; in US Patent Appl. Publ. Nos. 2007/0178095; 2010/0166764; 2009/0148436; and International Patent Appl. Publ. No. WO 2010/070094. Anti-GDF8 antibodies are also described in U.S. patent application Ser. No. 13/115,170, filed on May 25, 2011, and published as US 2011/0293630, including the antibodies designated 8D12, H4H1657N2, and H4H1669P. Any of the anti-GDF8 antibodies mentioned and/or described in any of the foregoing patents or publications, or antigen-binding fragments thereof, can be used in the context of the present invention, so long as such antibodies and/or antigen-binding fragments "specifically bind" GDF8, as that expression is defined herein.

Table 1 sets forth the sequence identifiers of the HCVRs, LCVRs, and CDRs of certain non-limiting, exemplary anti-GDF8 antibodies that can be used in the context of the present invention.

Pharmaceutical Compositions and Methods of Administration

The present invention includes pharmaceutical compositions comprising a GDF8-specific binding protein and an Activin A-specific binding protein. The present invention also includes pharmaceutical compositions comprising an antigen-binding molecule comprising a GDF8-specific binding domain and an Activin A-specific binding domain. The pharmaceutical compositions of the invention are formulated with suitable carriers, excipients, and other agents that provide suitable transfer, delivery, tolerance, and the like. A multitude of appropriate formulations can be found in, e.g., Remington's Pharmaceutical Sciences, Mack Publishing Company, Easton, Pa. Suitable formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Additional suitable formulations are also described in Powell et al. "Compendium of excipients for parenteral formulations" PDA (1998) J Pharm Sci Technol 52:238-311.

Various delivery systems are known and can be used to administer the pharmaceutical compositions of the present invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The compositions may

TABLE 1

| Antibody | HCVR | HCDR1 | HCDR2 | HCDR3 | LCVR | LCDR1 | LCDR2 | LCDR3 |
|---|---|---|---|---|---|---|---|---|
| 8D12 | 1 | 2 | 3 | 4 | 5 | 6 | 7 | 8 |
| H4H1657N2 | 9 | 10 | 11 | 12 | 13 | 14 | 15 | 16 |
| H4H1669P | 17 | 18 | 19 | 20 | 21 | 22 | 23 | 24 |

Anti-Activin A Antibodies and Antigen-Binding Fragments Thereof

In certain specific embodiments of the present invention, the Activin A-specific binding protein, or the Activin A-specific binding domain, comprises or consists of an antibody or antigen-binding fragment thereof that specifically binds Activin A. In certain embodiments, the Activin A-specific binding protein specifically binds the βA subunit. An antigen-specific binding protein that specifically binds the βA subunit may recognize both Activin A (βA/βA homodimer) and Activin AB (βA/βB heterodimer). Thus, according to the present invention, an Activin A-specific binding protein may bind both Activin A and Activin AB (but not Activin B). Anti-Activin A antibodies are mentioned in, e.g., US Patent Appl. Publ. No 2009/0234106. A particular anti-Activin A antibody is designated "MAB3381," and is available commercially from R&D Systems, Inc, Minneapolis, Minn. MAB3381 specifically binds Activin A (homodimer) as well as Activin AB (heterodimer). Any of the aforementioned anti-Activin A antibodies, or antigen-binding fragments thereof, can be used in the context of the present invention, so long as such antibodies and/or antigen-binding fragments "specifically bind" Activin A and/or Activin AB, as defined herein.

be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical compositions of the present invention can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of active ingredient (e.g., anti-GDF8 antibodies and anti-Activin A antibodies) that can be administered to a subject is, generally, a therapeutically effective amount. As used herein, the phrase "therapeutically effective amount" means a dose of antigen-specific binding proteins and/or antigen-binding molecules that results in a detectable increase in one or more of the following parameters: body weight, muscle mass (e.g., tibialis anterior [TA] muscle mass, gastrocnemius [GA] muscle mass, quadriceps [Quad] muscle mass, etc.), muscle strength/power, and/or muscle function. For example, a "therapeutically effective amount" of a GDF8-specific binding protein and/or an Activin A-specific binding protein includes, e.g., an amount of GDF8-specific binding protein and/or Activin A-specific binding protein that, when administered to a test subject, causes an increase in TA or GA muscle mass of at least 2%, 5%, 10%, 15%, 20%, 25%, 30%, 40%, 50%, 60% or more, compared to control treated subjects, e.g., as illustrated in Example 1, herein.

In the case of antibodies of the present invention (e.g., anti-GDF8 antibodies, anti-Activin A antibodies, or bispecific antibodies that specifically bind GDF8 and Activin A), a therapeutically effective amount can be from about 0.05 mg to about 600 mg; e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the respective antibody.

The amount of antibody of the present invention (e.g., anti-GDF8 antibodies, anti-Activin A antibodies, or bispecific antibodies that specifically bind GDF8 and Activin A) contained within the individual doses may be expressed in terms of milligrams of antibody per kilogram of patient body weight (i.e., mg/kg). For example, the anti-GDF8, anti-Activin A and/or anti-GDF8/anti-Activin A bispecific antibodies of the present invention may be administered to a patient at a dose of about 0.0001 to about 50 mg/kg of patient body weight (e.g. 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 10.5 mg/kg, 11.0 mg/kg, 11.5 mg/kg, etc.).

The compositions of the present invention may comprise equal amounts of GDF8-specific binding protein and Activin A-specific binding protein. Alternatively, the amount of GDF8-specific binding protein in the composition may be less than or greater than the amount of Activin A-specific binding protein. A person of ordinary skill in the art, using routine experimentation, will be able to determine the appropriate amounts of the individual components in the compositions of the present invention necessary to produce a desired therapeutic effect.

Therapeutic Methods

The present invention includes methods of treating conditions or afflictions which can be cured, alleviated or improved by increasing muscle strength/power and/or muscle mass and/or muscle function in an individual, or by favorably altering metabolism (carbohydrate, lipid and protein processing) by specifically binding GDF8, and/or Activin A, and/or Activin AB, and not binding other ActRIIB ligands. For example, the present invention includes methods for increasing muscle strength/power and/or muscle mass and/or muscle function in a subject, or for treating a disease or disorder characterized by decreased muscle mass or strength in a subject, by administering to the subject an Activin A-specific binding protein. The present invention also includes methods for increasing muscle strength/power and/or muscle mass and/or muscle function in a subject, or for treating a disease or disorder characterized by decreased muscle mass or strength in a subject, by administering to the subject a GDF8-specific binding protein and an Activin A-specific binding protein. Any of the GDF8-specific binding proteins and/or Activin A-specific binding proteins disclosed or referred to herein can be used in the context of these aspects of the invention. For example, the therapeutic methods of the present invention include administering to a subject an anti-GDF8 antibody and/or an anti-Activin A antibody.

In methods which comprise administering a GDF8-specific binding protein and an Activin A-specific binding protein to a subject, the GDF8-specific binding protein and the Activin A-specific binding protein may be administered to the subject at the same or substantially the same time, e.g., in a single therapeutic dosage, or in two separate dosages which are administered simultaneously or within less than about 5 minutes of one another. Alternatively, the GDF8-specific binding protein and the Activin A-specific binding protein may be administered to the subject sequentially, e.g., in separate therapeutic dosages separated in time from one another by more than about 5 minutes.

The present invention also includes methods for increasing muscle strength/power and/or muscle mass and/or muscle function in a subject, or for treating a disease or disorder characterized by decreased muscle mass or strength in a subject, by administering to the subject an antigen-binding molecule comprising a GDF8-specific binding domain and an Activin A-specific binding domain. Any of the antigen-binding molecules disclosed or referred to herein can be used in the context of this aspect of the invention. For example, the therapeutic methods of the present invention include administering to a subject a bispecific antibody comprising a first variable domain comprising a HCVR/LCVR pair that specifically binds GDF8 and a second variable domain comprising a HCVR/LCVR pair that specifically binds Activin A.

The compositions of the present invention may be administered to a subject along with one or more additional therapeutic agents, including, e.g., growth factor inhibitors, immunosuppressants, anti-inflammatory agents, metabolic inhibitors, enzyme inhibitors, and cytotoxic/cytostatic agents. The additional therapeutic agent(s) may be administered prior to, concurrent with, or after the administration of the GDF8- and Activin A-specific binding proteins of the present invention.

Exemplary diseases, disorders and conditions that can be treated with the compositions of the present invention include, but are not limited to, sarcopenia, cachexia (either idiopathic or secondary to other conditions, e.g., cancer, chronic renal failure, or chronic obstructive pulmonary disease), muscle injury, muscle wasting and muscle atrophy, e.g., muscle atrophy or wasting caused by or associated with disuse, immobilization, bed rest, injury, medical treatment or surgical intervention (e.g., hip fracture, hip replacement, knee replacement, etc.) or by necessity of mechanical ventilation. The compositions of the invention may also be used to treat, prevent or ameliorate diseases such as cancer, obesity, diabetes, arthritis, multiple sclerosis, muscular dystrophy, amyotrophic lateral sclerosis, Parkinson's disease, osteoporosis, osteoarthritis, osteopenia, metabolic syndromes (including, but not limited to diabetes, obesity, nutritional disorders, organ atrophy, chronic obstructive pulmonary disease, and anorexia).

Avoidance of Side Effects

The present invention includes methods for increasing muscle strength/power and/or muscle mass and/or muscle function in a subject, or for treating a disease or disorder characterized by decreased muscle mass or strength in a subject, without causing adverse side effects associated with the administration of molecules which bind multiple (e.g., 3 or more) ActRIIB ligands. For example, the clinical molecule referred to as ACE-031 (Acceleron Pharma, Inc., Cambridge, Mass.) is a multimer consisting of the extracellular portion of ActRIIB fused to an IgG Fc domain (this molecule is also referred to herein as "ActRIIB-Fc"). ActRIIB-Fc binds GDF8 as well as other ActRIIB ligands such as, e.g., Activin A, Activin B, GDF11, BMP9, BMP10, and TGFβ, and is known to cause various adverse side effects when administered to human patients. Significantly, the present inventors have unexpectedly discovered that specifically inhibiting GDF8 and Activin A (e.g., by administering an anti-GDF8 antibody and an anti-Activin A antibody), while not inhibiting other ActRIIB ligands such as Activin B, GDF11, BMP9, BMP10, and TGFβ, results in an increase in muscle mass that is at least equivalent to that observed by administration of ActRIIB-Fc, without causing the adverse side effects associated with non-specific Activin binding agents such as ActRIIB-Fc.

Administration Regimens

According to certain embodiments of the present invention, multiple doses of the compositions of the present invention (e.g., compositions comprising GDF8- and/or Activin A-specific binding proteins or antigen-binding molecules comprising a GDF8-specific binding domain and an Activin A-specific binding domain), may be administered to a subject over a defined time course. The methods according to this aspect of the invention comprise sequentially administering to a subject multiple doses of the compositions of the present invention. As used herein, "sequentially administering" means that each dose of the compositions of the present invention are administered to the subject at a different point in time, e.g., on different days separated by a predetermined interval (e.g., hours, days, weeks or months). The present invention includes methods which comprise sequentially administering to the patient an initial dose of a composition of the present invention, followed by one or more secondary doses of the composition, and optionally followed by one or more tertiary doses of the composition.

The terms "initial dose," "secondary doses," and "tertiary doses," refer to the temporal sequence of administration of the compositions of the present invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of active ingredient(s), but will generally differ from one another in terms of frequency of administration. In certain embodiments, however, the amount of active ingredient(s) contained in the initial, secondary and/or tertiary doses will vary from one another (e.g., adjusted up or down as appropriate) during the course of treatment.

In one exemplary embodiment of the present invention, each secondary and/or tertiary dose is administered 1 to 30 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more) days after the immediately preceding dose. The phrase "the immediately preceding dose," as used herein, means, in a sequence of multiple administrations, the dose(s) of the compositions of the present invention which are administered to a subject prior to the administration of the very next dose in the sequence with no intervening doses.

The methods according to this aspect of the invention may comprise administering to a patient any number of secondary and/or tertiary doses of the compositions of the present invention. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 29 days after the immediately preceding dose. Similarly, in embodiments involving multiple tertiary doses, each tertiary dose may be administered at the same frequency as the other tertiary doses. For example, each tertiary dose may be administered to the patient 1 to 60 days after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Specific Inhibition of GDF8 and Activin A Causes Synergistic Increases in Skeletal Muscle Mass Introduction ActRIIB-Fc is a GDF8 antagonist consisting of the extracellular portion of the ActRIIB receptor, stabilized by fusion to an IgG Fc domain. ActRIIB-Fc has been shown to increase muscle mass in mice to a greater extent than anti-GDF8 antibodies. The present inventors hypothesized that the enhanced activity of ActRIIB-Fc could potentially be due to its ability to bind additional ActRIIB ligands besides GDF8. In particular, it was proposed that antagonism of Activin A, in addition to antagonism of GDF8, might cause greater increases in skeletal muscle mass than what has been observed in animals treated with anti-GDF8 antibodies alone. Thus, the present Example was designed to determine whether specific inhibition of GDF8 and Activin A can increase skeletal muscle mass to an extent that is at least equivalent to the increase observed using ActRIIB-Fc.

Results and Discussion

The extent of skeletal muscle hypertrophy induced by administration of ActRIIB-Fc was compared to the effect of administration of a GDF8-specific antibody, an Activin A specific antibody, or a combination of an anti-GDF8+anti-Activin A antibody. The ActRIIB-Fc construct used in this Example has the amino acid sequence of SEQ ID NO:27. The anti-GDF8 antibody used in this Example is the antibody designated H4H1657N2 (see Table 1). The anti-Activin A antibody used in this Example is the antibody designated MAB3381 (available from R&D Systems, Inc., Minneapolis, Minn.). An isotype-matched (hIgG4) antibody was used as negative control.

Briefly, 25 male CB17 SCID mice at approximately 10 weeks of age, were divided evenly according to body weight into 5 groups based on treatment (Isotype Control mAb, ActRIIB-Fc, H4H1657N2, MAB3381, or H4H1657N2+MAB3381). Reagents were administered subcutaneously at a dose of 10 mg/kg twice for the first week (on day 0 and day 3) and once a week for the following three weeks (on day 7, day 14 and day 21). On day 28, mice were euthanized and weighed, and the tibialis anterior (TA) muscles, and the gastrocnemius (GA) muscles, were dissected and weighed. Tissues were normalized to starting body weight, and percent change in weight over the isotype-matched (hIgG4) control antibody was calculated. Results are summarized in Table 2 and are expressed as percent increase over negative control±standard error of the mean.

TABLE 2A

|  | Isotype Control | ActRIIB-Fc | H4H1657N2 (anti-GDF8) | MAB3381 (Anti-Activin A) | H4H1657N2 + MAB3381 |
| --- | --- | --- | --- | --- | --- |
| Dose | 10 mg/kg | 10 mg/kg | 10 mg/kg | 10 mg/kg | 10 mg/kg (each) |
| Body Weight | 0.00 ± 1.18 | 14.83 ± 4.36 | 7.88 ± 2.10 | 4.52 ± 1.02 | 16.08 ± 1.91 |
| TA Muscle | 0.00 ± 2.90 | 44.88 ± 5.35 | 22.42 ± 1.65 | 19.09 ± 2.04 | 55.13 ± 5.16 |
| GA Muscle | 0.00 ± 2.13 | 34.25 ± 6.97 | 24.17 ± 1.84 | 14.02 ± 0.91 | 41.72 ± 3.63 |

In order to confirm that muscle hypertrophy was the result of an increase in muscle fiber size, the tibialis anterior (TA) muscle was embedded in OCT and isopentane-frozen for histological examination and immunohistochemical labeling. Cross-sections of the TA muscle were stained with anti-laminin antibody to outline the muscle fiber, and the average cross-sectional-area (CSA) was determined by using an imaging analysis system. Results of two independent experiments (Exp#1 and Exp#2) are summarized in Table 2B. All data are expressed as means±the standard error of the mean.

TABLE 2B

|  | Isotype Control | ActRIIB-Fc | H4H1657N2 (anti-GDF8) | MAB3381 (Anti-Activin A) | H4H1657N2 + MAB3381 |
|---|---|---|---|---|---|
| CSA (μm$^2$) Exp#1 | 1800.1 ± 78.3 | 2488.7 ± 116.6 | 1987.2 ± 72.1 | 1962.6 ± 157.1 | 2435.4 ± 119.7 |
| CSA (μm$^2$) Exp#2 | 1702.7 ± 50.9 | 2571.9 ± 123.3 | 2006.3 ± 133.9 | 1690.9 ± 78.9 | 2452.6 ± 110.3 |

As shown in Table 2A, ActRIIB-Fc induced significant hypertrophy in all muscles examined, with increases of 44.88±5.35% in TA muscle mass, and 34.25±6.97% in GA muscle mass. Treatment with H4H1657N2 (anti-GDF8), or MAB3381 (anti-Activin A) alone also induced significant hypertrophy in TA muscle mass (22.42±1.65% and 19.09±2.04%, respectively) and GA muscle mass (24.17±1.84 and 14.02±0.91%, respectively) but not as pronounced as ActRIIB-Fc. However, the combination of H4H1657N2 and MAB3381 induced increases in TA (55.13±5.16%) and GA (41.72±3.63%), that were even greater than what was observed in ActRIIB-hFc-treated animals. Furthermore, it was confirmed that the muscle hypertrophy observed was the result of an increase in muscle fiber size (see Table 2B).

Importantly, the extent of increases in body weight, TA muscle, and GA muscle for the anti-GDF8+anti-Activin A combination were substantially greater than the sums of the increases in these parameters observed in the anti-GDF8 plus anti-Activin A monotherapy subjects. Thus, combined inhibition of GDF8 and Activin A produces synergistic increases in body weight and skeletal muscle mass, and these increases are more pronounced than what is observed in ActRIIB-Fc-treated animals. Moreover, as demonstrated in the following Example, the increases in body weight and skeletal muscle mass in animals that are treated with GDF8- and Activin A-specific binding agents, can be achieved without causing the adverse side effects observed with molecules such as ActRIIB-Fc.

Example 2: Specific Antagonism of GDF8 and Activin A does not Cause Adverse Side Effects Associated with Non-Specific Activin Ligand Binding Agents

Background

ActRIIB-Fc binds multiple ActRIIB ligands and causes significant side effects. The present Example demonstrates that the adverse side effects associated with ActRIIB-Fc can be avoided by selectively antagonizing only certain ActRIIB ligands, namely GDF8 and/or Activin A. In particular, biomarker, protein expression studies, and in vivo red blood cell characteristics (i.e., elevated endoglin levels and increased red cell distribution width), which appear to be linked to ActRIIB-Fc side effects in humans, were only seen in animals treated with ActRIIB-Fc, but not in animals treated with anti-GDF8 antibody, anti-Activin A antibody or a combination of anti-GDF8 and anti-Activin A antibodies. Thus, taken together, the results below show that specific antagonism of GDF8 and/or Activin A, without antagonizing other ActRIIB ligands such as Activin B, GDF11, BMP9, BMP10, and/or TGFβ, does not cause the undesired phenotypes associated with ActRIIB-Fc.

Results and Discussion

Hematology studies were conducted using mice treated with ActRIIB-Fc (SEQ ID NO:27), H4H1657N2 (anti-GDF8), MAB3381 (anti-Activin A), or a combination of H4H1657N2+MAB3381 according to the dosing schedule described in Example 1 (i.e., 10 mg/kg twice for the first week [on day 0 and day 3] and once a week for the following three weeks [on day 7, day 14 and day 21]). Specifically, hemoglobin levels and red blood cell distribution width (RDVV) (an indicator of certain blood disorders such as anemia) were measured from blood samples taken from mice treated with the various agents. RDW results (normalized to Isotype Control values) are summarized in Table 3.

TABLE 3

|  | Isotype Control | ActRIIB-Fc | H4H1657N2 (anti-GDF8) | MAB3381 (Anti-Activin A) | H4H1657N2 + MAB3381 |
|---|---|---|---|---|---|
| Dose | 10 mg/kg | 10 mg/kg | 10 mg/kg | 10 mg/kg | 10 mg/kg (each) |
| % RDW | 0.0 ± 1.8 | 19.1 ± 2.1 | −1.6 ± 0.7 | 4.4 ± 0.5 | −1.9 ± 1.2 |

After 28 days of treatment, none of the groups had a significant increase in Hb levels. However, as shown in Table 3, mice treated with ActRIIB-Fc showed a significant increase in red blood cell distribution width (RDW), which reflects the extent of size variation of red blood cells in a sample. Surprisingly, mice treated with anti-GDF8 antibody, anti-Activin A antibody, or the combination of anti-GDF8+anti-Activin A antibodies, did not exhibit an appreciable degree of increase in % RDW as compared to isotype control-treated mice. These experiments therefore demonstrate that antagonism of GDF8 or Activin A alone, or the combination of anti-GDF8 antibody+anti-Activin A antibodies, do not cause the hematological phenotypes that are observed with ActRIIB-Fc treatment.

To further investigate the differences in side effects between ActRIIB-Fc-treated subjects and anti-GDF8+anti-Activin A combination-treated subjects, microarray and protein expression studies were conducted.

Microarray analysis was conducted on skeletal muscle samples from mice treated with isotype control, ActRIIB-Fc, and H4H1657N2 (anti-GDF8). From these experiments, a set of genes was identified that is uniquely affected by ActRIIB-Fc. Of particular interest was the up-regulation of Endoglin mRNA levels in skeletal muscle in samples from ActRIIB-Fc-treated subjects. Endoglin is a transmembrane protein expressed primarily in endothelial cells and interacts and promotes signaling through receptors of the TGFβ family (ALK1) in response to TGFβ, BMP9, or BMP10. Signaling mediated by Alk1 and Endoglin in endothelial cells is required for maintaining normal vascular structures. Mutations in the Alk1 and Endoglin genes in humans causes Hereditary Haemorrhagic Talangiectasia (HHT). Patients suffering HHT display a vascular phenotype including dilated blood vessels, and bleeding in the nasal, oral, and gastrointentinal mucosa. Thus, elevated Endoglin levels caused by ActRIIB-Fc potentially reflect at least some of the adverse side effects observed in patients treated with this therapeutic agent.

Next, experiments were conducted to confirm that the changes observed in Endoglin mRNA levels were also reflected at the protein expression level using muscle samples from the previous experiment. Quantitative Western blot analysis of Endoglin protein levels was conducted on samples from mice treated with isotype control, ActRIIB-Fc, H4H1657N2 (anti-GDF8), MAB3381 (anti-Activin A), and the H4H1657N2+MAB3381 combination. Expression of Endoglin was normalized by the endothelial cell marker CD31 to confirm that ActRIIB-hFc treatment does not increase the endothelial compartment. Results (normalized to Isotype Control values) are summarized in Table 4.

TABLE 4

|  | Isotype Control | ActRIIB-Fc | H4H1657N2 (anti-GDF8) | MAB3381 (Anti-Activin A) | H4H1657N2 + MAB3381 |
|---|---|---|---|---|---|
| Dose | 10 mg/kg | 10 mg/kg | 10 mg/kg | 10 mg/kg | 10 mg/kg (each) |
| Endoglin O.D. | 0.0 ± 1.4 | 88.4 ± 2.9 | 5.5 ± 2.1 | 4.7 ± 5.0 | 1.4 ± 7.6 |
| CD31 O.D. | 0.0 ± 4.2 | 2.2 ± 6.2 | −6.8 ± 4.0 | −2.1 ± 9.3 | −19.3 ± 6.7 |
| O.D. Ratio | 0.0 ± 5.6 | 84.5 ± 8.3 | 13.1 ± 2.6 | 7.1 ± 5.1 | 25.5 ± 1.0 |

As shown in Table 4, levels of Endoglin protein were significantly elevated in the ActRIIB-hFc group, but not in the anti-GDF8 or anti-Activin A-treated groups. Interestingly, Endoglin levels were also not elevated in the anti-GDF8+anti-Activin A combination-treated group.

Summary and Conclusions

The results presented in the prior Example (Example 1) show that the combination of anti-GDF8+anti-Activin A treatment can produce muscle hypertrophy effects that are at least equivalent to those observed with ActRIIB-Fc treatment. The present Example 2 shows that indicators of the adverse side effects of ActRIIB-Fc treatment, such as increased RDW and elevated Endoglin expression, are not observed with anti-GDF8, anti-Activin A, or anti-GDF8+ anti-Activin A combination treatment. Thus, the present inventors have surprisingly discovered that treatment with a GDF8-specific binding protein, or an Activin A-specific binding protein, or a combination of a GDF8-specific binding protein and an Activin A-specific binding protein provide highly efficacious methods for increasing muscle mass and strength that avoid the adverse side effects caused by ActRIIB-Fc.

Example 3: Effects of GDF8 and Activin A Antagonists on Wound Healing

Pharmaceutical agents which function to increase muscle mass and strength, such as GDF8 antagonists and Activin A antagonists, have utility in settings in which patients have undergone surgery (or will undergo surgery), e.g., for joint replacement or repair, etc. As such, agents that are administered to promote the rescue of muscle mass would ideally not interfere with other aspects of surgical recovery such as wound healing.

Accordingly, experiments were conducted to determine the effects of GDF8 blockade, Activin A blockade, and combinations thereof, on wound healing, as compared to the effects of ActRIIB-Fc treatment. These studies were carried out in SCID mice. In particular, the effects of H4H1657N2 (anti-GDF8) and MAB3381 (anti-Activin A) administration on wound healing, as single treatments or in combination with one another, were compared to the wound healing effects of the more broadly-acting decoy receptor ActRIIB-hFc (SEQ ID NO:27). Briefly, circular skin excisional wounds were made on the left abdominal flank of 30 male SCID mice approximately 7-8 weeks. The animals were divided into five treatment groups (n=6 per group) each receiving five subcutaneous injections of an isotype control antibody, ActRIIB-hFc, H4H1657N2, MAB3381, or H4H1657N2+MAB3381. All reagents were administered at 10 mg/kg every 3-4 days. The first dose was given the day before wounding the animals, and the last one was given two days before terminating the study on day 14. Digital images of the wound were taken on day 0 (day of wounding), 6, 9, 12, and 14, and the excision wound size change was measured and compared to the isotype control group. Results are summarized in Table 5. All data are expressed as mean total wound size±the standard error of the mean.

TABLE 5

| Treatment (10 mg/kg every 3-4 days) | Days After Wounding (total wound size mm$^2$) | | | | |
|---|---|---|---|---|---|
| | Day 0 | Day 6 | Day 9 | Day 12 | Day 14 |
| Isotype control | 59.95 ± 2.25 | 31.92 ± 3.43 | 18.75 ± 3.67 | 9.46 ± 2.25 | 7.66 ± 1.51 |
| ActRIIB-hFc | 61.30 ± 1.78 | 49.07 ± 2.74 | 30.50 ± 2.74 | 17.60 ± 1.53 | 14.90 ± 1.25 |
| H4H1657N2 (anti-GDF8) | 64.98 ± 2.56 | 30.69 ± 5.3 | 16.36 ± 3.27 | 7.71 ± 1.93 | 6.98 ± 1.32 |
| MAB3381 (anti-Activin A) | 62.07 ± 2.94 | 35.58 ± 4.96 | 23.38 ± 3.3 | 13.67 ± 2.19 | 11.01 1.45 |
| H4H1657N2 + MAB3381 | 61.08 ± 2.54 | 31.85 ± 2.83 | 17.68 ± 2.17 | 10.89 ± 1.74 | 9.09 ± 1.4 |

An analysis of wound size at the end of the experiment, as shown in Table 5, revealed that treatment with H4H1657N2, MAB3381, or H4H1657N2+MAB3381 resulted in no significant difference in wound size at any time after the initial excision as compared to the isotype control group. By contrast, ActRIIB-hFc significantly delayed wound closure as indicated by the larger wound size at days 6, 9, 12, and 14 as compared to the wound size in mice treated with H4H1657N2, MAB3381, H4H1657N2+ MAB3381, or the isotype control.

This experiment demonstrates that therapeutic treatments involving GDF8 antagonism, Activin A antagonism, or GDF8+Activin A dual antagonism, do not significantly impair wound healing, whereas the less specific antagonist ActRIIB-hFc does significantly impair wound healing. Accordingly, the present Example provides further support for the notion that specific antagonism of GDF8 and Activin A can produce enhanced muscle mass and function, similar to what is seen with ActRIIb-hFc treatment, but without the adverse side effects associated with ActRIIb-hFc treatment.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A composition comprising a GDF8-specific binding protein and an Activin A-specific binding protein, wherein the GDF8-specific binding protein is a human anti-GDF-8 antibody or antigen-binding fragment thereof that specifically binds GDF-8 and inhibits GDF-8, and wherein the Activin A-specific binding protein is an anti-Activin A antibody or antigen-binding fragment thereof that inhibits Activin A, wherein the anti-GDF8 antibody or antigen-binding fragment thereof comprises the heavy chain complementarity determining regions (HCDRs) of a heavy chain variable region (HCVR) comprising an amino acid sequence selected from the group consisting of SEQ ID NO: 1, 9, and 17, and the light chain complementarity determining regions (LCDRs) of a light chain variable region (LCVR) selected from the group consisting of SEQ ID NO: 5, 13, and 21.

2. The composition of claim 1, wherein the anti-GDF8 antibody or antigen-binding fragment thereof comprises three HCDRs comprising SEQ ID NO:10, SEQ ID NO:11, and SEQ ID NO:12, and three LCDRs comprising SEQ ID NO:14, SEQ ID NO:15, and SEQ ID NO:16.

3. An antigen-binding molecule comprising a human anti-GDF8 antibody or antigen-binding fragment thereof that specifically binds GDF-8 and inhibits GDF-8 and an anti-Activin A antibody or antigen-binding fragment thereof that inhibits Activin A, wherein the anti-GDF8 antibody or antigen-binding fragment thereof comprises the HCDRs of a HCVR comprising an amino acid sequence selected from the group consisting of SEQ ID NO: 1, 9, and 17, and the LCDRs of a LCVR comprising an amino acid sequence selected from the group consisting of SEQ ID NO: 5, 13, and 21.

4. The antigen-binding molecule of claim 3, wherein the anti-GDF8 antibody or antigen binding fragment comprises a heavy chain variable region (HCVR) and a light chain variable region (LCVR) and/or the anti-Activin A antibody or antigen-binding fragment comprises a heavy chain variable region (HCVR) and a light chain variable region (LCVR).

5. The antigen-binding molecule of claim 4, wherein the HCVR of the anti-GDF8 antibody or antigen-binding fragment comprises three heavy chain complementarity determining regions (HCDRs) comprising SEQ ID NO:10, SEQ ID NO:11, and SEQ ID NO:12, and wherein the LCVR of the anti-GDF8 antibody or antigen-binding fragment comprises three light chain complementarity determining regions (LCDRs) comprising SEQ ID NO:14, SEQ ID NO:15, and SEQ ID NO:16.

6. The antigen-binding molecule of claim 4, wherein antigen-binding molecule is a bispecific antibody.

7. A method for increasing muscle mass or strength in a subject, the method comprising administering to the subject a GDF8-specific binding protein and an Activin A-specific binding protein, wherein the GDF8-specific binding protein is a human anti-GDF8 antibody or antigen-binding fragment thereof that specifically binds GDF8 and inhibits GDF8, and wherein the Activin-A-specific binding protein is an anti-Activin A antibody or antigen-binding fragment thereof that inhibits Activin A, wherein the anti-GDF8 antibody or antigen-binding fragment thereof comprises the HCDRs of a HCVR comprising an amino acid sequence selected from the group consisting of SEQ ID NO: 1, 9, and 17, and the LCDRs of a LCVR comprising an amino acid sequence selected from the group consisting of SEQ ID NO: 5, 13, and 21.

8. The method of claim 7, wherein the anti-GDF8 antibody or antigen-binding fragment thereof comprises three HCDRs comprising SEQ ID NO:10, SEQ ID NO:11, and SEQ ID NO:12, and three LCDRs comprising SEQ ID NO:14, SEQ ID NO:15, and SEQ ID NO:16.

9. A method for increasing muscle mass or strength in a subject, the method comprising administering to the subject an antigen-binding molecule comprising a hum anti-GDF8-specific antibody or antigen-binding fragment thereof that specifically binds GDF8 and inhibits GDF-8 and an Activin A-specific antibody or antigen-binding fragment thereof that inhibits Activin A, wherein the anti-GDF8 antibody or antigen-binding fragment thereof comprises the HCDRs of a HCVR comprising an amino acid sequence selected from the group consisting of SEQ ID NO: 1, 9, and 17, and the LCDRs of a LCVR comprising an amino acid sequence selected from the group consisting of SEQ ID NO: 5, 13, and 21.

10. The method of claim 9, wherein the anti-GDF8 antibody or antigen-binding fragment thereof comprises three heavy chain complementarity determining regions (HCDRs) comprising SEQ ID NO:10, SEQ ID NO:11, and SEQ ID NO:12, and three light chain complementarity determining regions (LCDRs) comprising SEQ ID NO:14, SEQ ID NO:15, and SEQ ID NO:16.

11. The method of claim 9, wherein the antigen-binding molecule is a bispecific antibody.

12. A method for treating a disease or disorder characterized by decreased muscle mass or strength, the method comprising administering to a subject in need thereof a composition comprising a GDF8-specific binding protein and an Activin A-specific binding protein, wherein the GDF8-specific binding protein is a human anti-GDF-8 antibody or antigen-binding fragment thereof that specifically binds GDF-8 and inhibits GDF-8, and wherein the Activin A-specific binding protein is an anti-Activin A antibody or antigen-binding fragment thereof that inhibits Activin A,
wherein the anti-GDF8 antibody or antigen-binding fragment thereof comprises the HCDRs of a HCVR comprising an amino acid sequence selected from the group consisting of SEQ ID NO: 1, 9 and 17, and the LCDRs of a LCVR comprising an amino acid sequence selected from the group consisting of SEQ ID NO: 5, 13, and 21.

13. A method for treating a disease or disorder characterized by decreased muscle mass or strength, the method comprising administering to a subject in need thereof an antigen-binding molecule comprising a human anti-GDF8 antibody or antigen-binding fragment thereof that specifically binds GDF8 and inhibits GDF-8 and an anti-Activin A antibody or antigen-binding fragment thereof that inhibits Activin A,
wherein the anti-GDF8 antibody or antigen-binding fragment thereof comprises the HCDRs of a HCVR comprising an amino acid sequence selected from the group consisting of SEQ ID NO: 1, 9, and 17, and the LCDRs of a LCVR comprising an amino acid sequence selected from the group consisting of SEQ ID NO: 5, 13, and 21.

14. The method of claim 12, wherein the anti-GDF8 antibody or antigen-binding fragment thereof comprises three HCDRs comprising SEQ ID NO: 10, SEQ ID NO: 11, and SEQ ID NO:12, and three LCDRs comprising SEQ ID NO:14, SEQ ID NO:15, and SEQ ID NO:16.

15. The method of claim 13, wherein the anti-GDF8 antibody or antigen binding fragment comprises a heavy chain variable region (HCVR) and a light chain variable region (LCVR) and/or the anti-Activin A antibody or antigen-binding fragment comprises a heavy chain variable region (HCVR) and a light chain variable region (LCVR).

16. The method of claim 15, wherein the HCVR of the anti-GDF8 antibody or antigen-binding fragment comprises three heavy chain complementarity determining regions (HCDRs) comprising SEQ ID NO:10, SEQ ID NO: 11, and SEQ ID NO:12, and wherein the LCVR of the anti-GDF8 antibody or antigen-binding fragment comprises three light chain complementarity determining regions (LCDRs) comprising SEQ ID NO:14, SEQ ID NO:15, and SEQ ID NO:16.

17. A method for treating a disease or disorder characterized by decreased muscle mass or strength, wherein the method comprises administrating to a subject a GDF8-specific binding protein and an Activin A-specific binding protein and wherein the GDF8-specific binding protein is a human anti-GDF-8 antibody or antigen-binding fragment thereof that specifically binds GDF-8 and inhibits GDF-8, and wherein the Activin A-specific binding protein is an anti-Activin A antibody or antigen-binding fragment thereof that inhibits Activin A,
wherein the anti-GDF8 antibody or antigen-binding fragment thereof comprises the HCDRs of a HCVR comprising an amino acid sequence selected from the group consisting of SEQ ID NO: 1, 9, and 17, and the LCDRs of a LCVR comprising an amino acid sequence selected from the group consisting of SEQ ID NO: 5, 13, and 21.

18. The method of claim 17, wherein the anti-GDF8 antibody or antigen-binding fragment thereof comprises three HCDRs comprising SEQ ID NO:10, SEQ ID NO:11, and SEQ ID NO:12, and three LCDRs comprising SEQ ID NO:14, SEQ ID NO:15, and SEQ ID NO:16.

* * * * *